United States Patent [19]

Pollack

[11] Patent Number: 4,854,328
[45] Date of Patent: Aug. 8, 1989

[54] ANIMAL MONITORING TELLTALE AND INFORMATION SYSTEM

[76] Inventor: Philip Pollack, 2644 W. Gregg Dr., Chandler, Ariz. 85224

[21] Appl. No.: 29,140

[22] Filed: Mar. 23, 1987

[51] Int. Cl.$^4$ ............................................... A61B 5/00
[52] U.S. Cl. .................................... 128/736; 128/903; 119/1; 340/539; 340/573; 340/870.17
[58] Field of Search ............... 128/736, 738, 903, 631; 340/573, 539, 870.16, 870.17; 119/1

[56] References Cited

U.S. PATENT DOCUMENTS

| | | | |
|---|---|---|---|
| 3,534,728 | 10/1970 | Barrows | 128/631 X |
| 3,774,594 | 11/1973 | Huszar | 128/903 |
| 3,781,837 | 12/1973 | Anderson et al. | 340/573 |
| 3,902,478 | 9/1975 | Konopasek et al. | 128/903 X |
| 3,960,140 | 6/1976 | Buxton | 128/903 |
| 3,971,362 | 7/1976 | Pope et al. | 128/631 |
| 4,262,632 | 4/1981 | Hanton et al. | 128/631 X |
| 4,625,733 | 12/1986 | Saynajakangas | 128/903 X |
| 4,651,750 | 3/1987 | Northeved | 128/903 X |

FOREIGN PATENT DOCUMENTS 2077473  12/1951  United Kingdom ................ 340/573

OTHER PUBLICATIONS

Pope et al., "A Wireless ... System", Med & Biol Eng, vol. 12, No. 3, pp. 348–354, May 1974.

*Primary Examiner*—Lee S. Cohen
*Attorney, Agent, or Firm*—Gregory J. Nelson

[57] ABSTRACT

An animal monitoring telltale device including a receiver attached to the animal and a transmitting device inserted in the animal subcutaneously or in a cavity at a location indicative of the deep body temperature of the animal. The implanted transmitter will send a signal to the proximately located receiver indicative of a monitored condition in the animal. In addition, the signal is encoded with an identification signal providing ownership information and theft protection. The receiver is preferably secured to an ear tag which tag includes a light or other visual signal indicative of a predetermined value of the measured condition. The receiver may also be operatively connected to a re-transmitter for re-transmitting a higher power signal to a remote monitoring location.

15 Claims, 3 Drawing Sheets

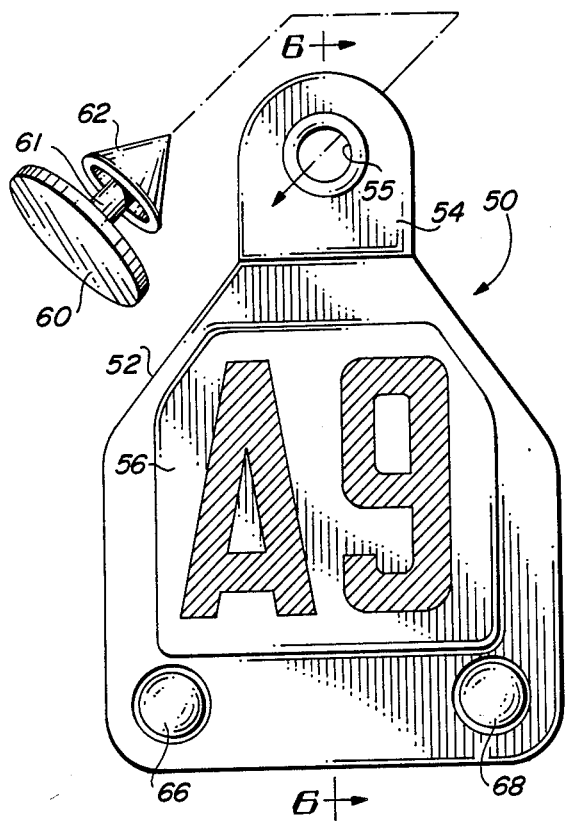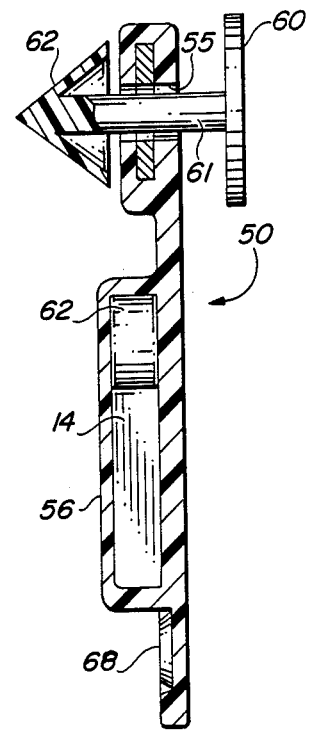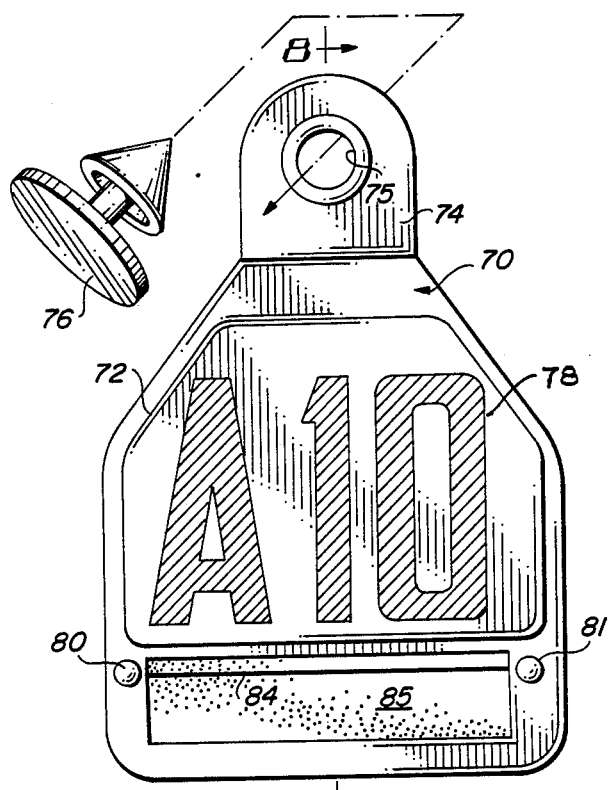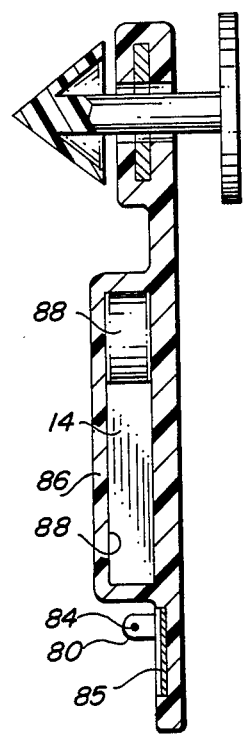

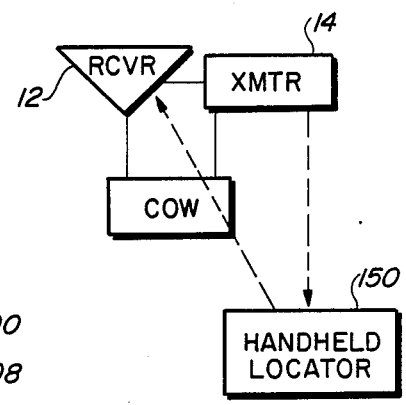
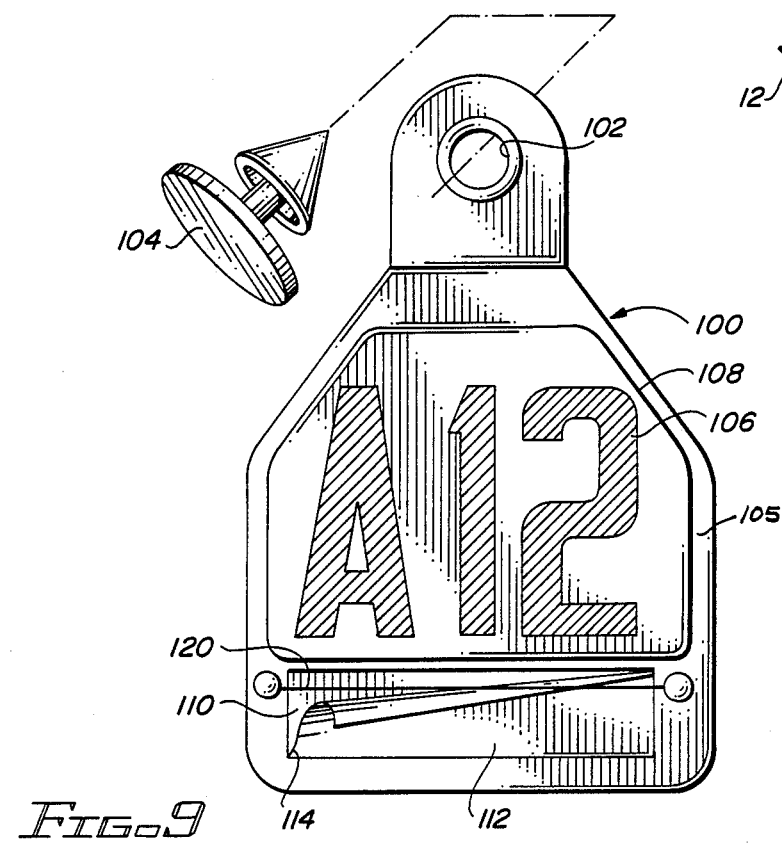
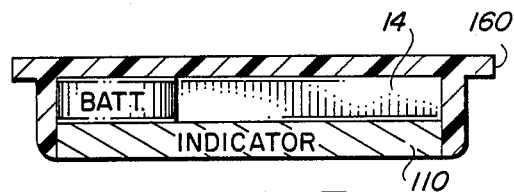
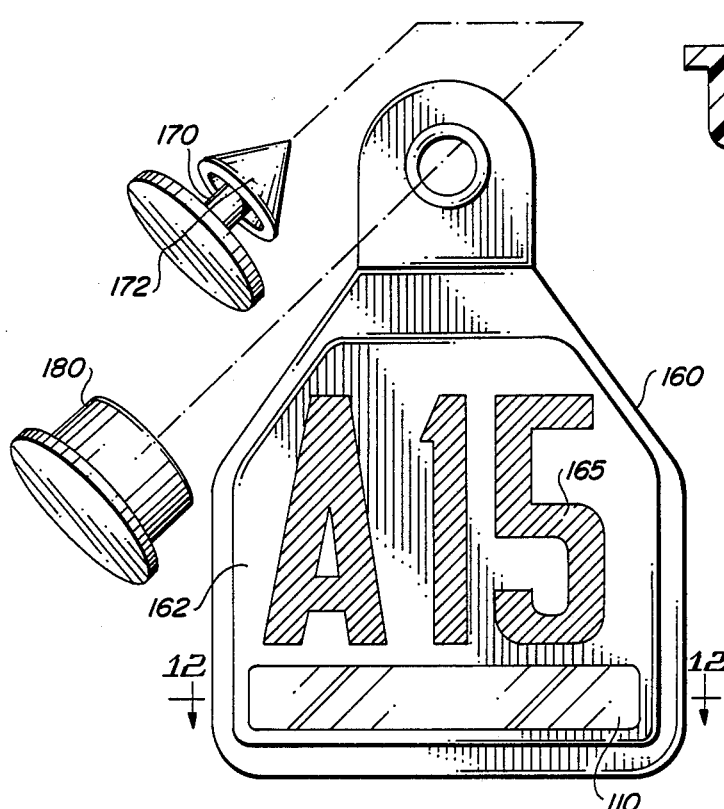
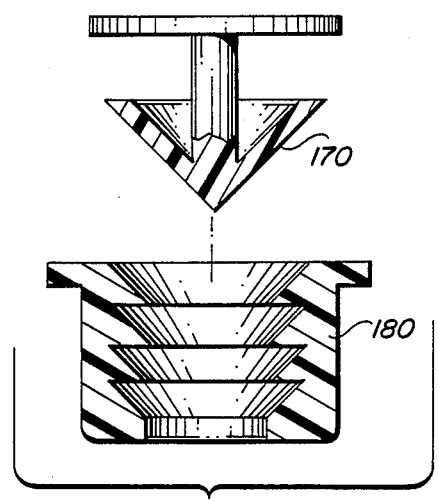

ANIMAL MONITORING TELLTALE AND INFORMATION SYSTEM

The present invention relates to a telltale monitoring system and more particularly relates to a telltale sensing and transmitting device which is implantable in an animal for monitoring a physiological condition of the animal and providing an informational signal which at a predetermined or threshold level actuates a visible or audible alarm observable at the animal and which may be re-transmitted to a remote location.

A particular problem in caring for livestock, particularly livestock maintained in large herds in corrals, cattle pens and feed lots, is the detection of a sick animal at an early stage of illness. In the past, detection was generally accomplished by visual observation of the herd. In such a situation, the experience and expertise of the individual observing the herd was important as only well-trained persons could detect ailing animals unless the animal was in an advanced stage of illness. By this time, the sick animal has exposed other animals in the close proximity of the herd possibly spreading the disease to others.

As a result of the problems of early detection of disease, various telemetry sensing devices, often termed "telltale" devices, have been provided in the prior art. These devices are helpful for determining a diseased condition in an animal and may also be used for indicating estrus in certain domestic animals. Generally these devices measure a physiological condition such as temperature which is indicative of the health or other condition of the animal.

Several prior art patents show the use of an encapsulated transmitter which is inserted or implanted in an animal which includes a temperature sensing device actuated transmitter. For example, the patent to Harvey, U.S. Pat. No. 3,583,389 shows such a device which is adapted to be inserted in the birth canal of an animal. U.S. Pat. No. 3,297,020 discloses an insertable electrical circuit for determining estrus.

U.S. Pat. No. 3,893,111 to Cotter discloses an encapsulated transmitter having a variable length antenna which length changes in accordance with the animal's body temperature. The device is embedded subcutaneously or implanted in the shoulder or hind quarter of the animal and the patentee suggests that the device is particularly practical for use by feed lot operators, cattle raisers and dairymen.

U.S. Pat. No. 4,083,364 to Kelly et al discloses the placement of a temperature sensor in the region behind the animal's ear adjacent to its skull.

The above systems have found only limited acceptability in the cattle industry for various reasons. One reason that temperature sensing devices which are either ingested by the animal or inserted in a bodily canal have not been widely used is that they are either difficult to insert and may become easily dislodged or expelled by the animal. Implantable devices which are inserted in an incision in the animal also present problems of dislodgement. Further, because devices of this type require an open incision in which the monitoring device is placed, the incision can become easily infected, thus, contributing to a diseased condition in the animal.

Accordingly, the present invention overcomes the deficiencies of the prior art. Briefly, the present invention comprises a transmitter and a receiver. The transmitter includes a physiological sensing device such as a temperature sensor and is contained in a small capsule-like housing with a suitable power supply and a transmitter. The capsule may be implanted in a suitable incision in the animal which incision heals over in a few days. The sensor monitors temperature and upon a predetermined limit or threshold value being reached, a signal indicative of the temperature of the animal is transmitted at low power and a low frequency. Other digitally coded information relating to the identity of the animal can also be transmitted by the implanted transmitter.

A receiver is positioned proximate the transmitter on the animal and typically would be contained in an ear tag attached to the animal. Because of the close proximity of the receiver to the implanted transmitter, low power noninterfering frequencies may be used. The receiver is operatively connected to provide an audio and/or visual indication of an elevated temperature condition. The visible display may be simply an LED which is lighted or the receipt of a signal may trigger a color change on the ear tag which is highly visible. In addition, the receiver may also incorporate a higher power transmitter for re-transmitting a signal to an off-site location which could be monitored and recorded at a central monitoring station.

Accordingly, it is a primary object of the present invention to provide an implantable animal monitoring telltale device including a transmitting device which is implantable in a cavity or incision in the animal and a proximately located receiving device on the animal which provides a visual and/or audible indication of a physiological parameter of the animal.

Another object of the present invention is to provide an implantable transmitter which emits a coded signal as part of the signal transmitted from within the animal which coded signal represents a unique identification number.

Another object of the present invention is to provide a system for locating a stray animal by triangulation from transmitted signals from the animal.

Another object of the present invention is to provide an implantable transmitter for animals which transmitter is retrievable and reusable and which may emit a radio frequency, induction, sonic, ultra sonic or other type of signal.

Another object of the present invention is to provide a sensing device and transmitter implantable in an animal which utilizes a low power range and which is encased in a non-toxic bio-acceptable housing.

Another object of the present invention is to provide a receiver located on an animal at a location such as an ear tag proximate the implanted transmitter, which receiver includes a re-transmitter for re-transmitting a signal indicative of a physiological condition of the animal and further including identification information to a remote source by radio frequency signal, a sonic signal or ultrasonic signal.

The above and other objects and advantages of the present invention will become more apparent from the following description, claims and drawings in which:

FIG. 5 is an exploded perspective view of a two-component animal tag incorporating the receiver components;

FIG. 6 is a sectional view taken along lines 6—6 of FIG. 5;

FIGS. 7 and 8 illustrate an alternate two-component animal tag with the receiver components and a visual indication;

FIG. 9 illustrates still another animal tag assembly with a receiver and a visual indicator;

FIG. 10 is a block diagram illustrating the use of the monitoring system as a locating system and FIGS. 11, 12 and 13 illustrate another type of ear tag assembly housing the receiver and indicator.

Figure 1:
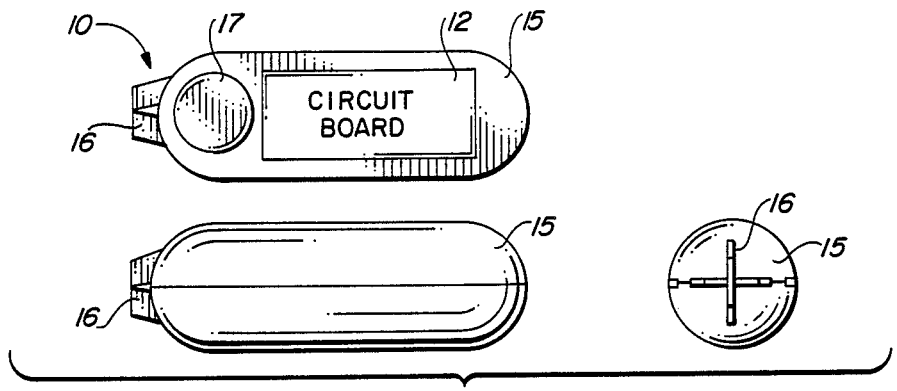
FIG. 1 is a view, partly schematic, of the encapsulated implantable sensor and transmitter.
Figure 2:
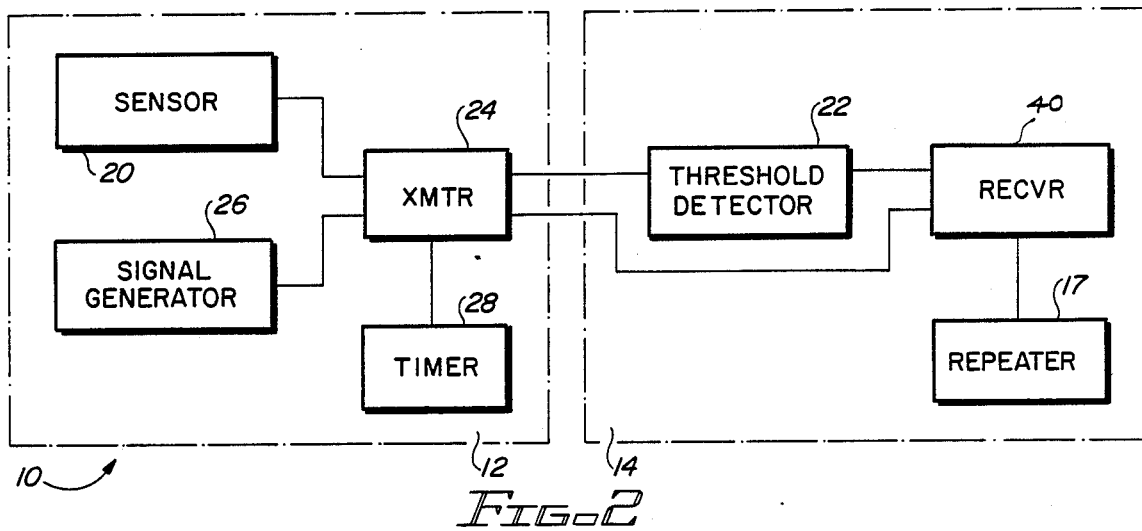
FIG. 2 is a block diagram representation of the transmitter and receiver showing the primary components thereof.

Turning now to the drawings, the preferred embodiment of the small low-powered radio transmitter is shown in FIGS. 1 and 2 and is generally designated by the numeral 10. The transmitter section 12 is enclosed or encased in a housing 15 which is a non-toxic, biomedically acceptable material suitable for implantation in an animal. For example, the material may be a latex rubber, medical grade ABS or other material suitable for this purpose and which may be sterilizable by known means. The capsule preferably is generally cylindrical in shape. The forward end of the capsule or housing may be provided with a sharpened leading edge 16 to facilitate insertion of the capsule subcutaneously or within an incision made for this purpose. The capsule contains a power source 17 which may be replaceable when the transmitter or capsule is removed from the animal. Preferably, the replacement of the power supply would be accomplished at a refurbishing location established for this purpose. The capsule also contains a small lower-powered transmitter and associated circuitry 12.

The transmitter and associated circuitry 12 can be embodied in a small circuit board enclosed within the capsule.

As shown in FIG. 2, the circuitry includes a physiological sensing device 20 for sensing temperature or other measurable parameters such as blood pressure, blood flow, pulse or the like. As shown, sensor 20 is a thermister which provides an output signal to low-power amplifier 24. An ID signal generator 26 provides a coded digital signal to transmitter 24 as, for example, a unique binary signal indicative of the identification number of the animal. A timer 28 controls the timing sequence of the circuit so that the transmitter 24 will transmit only at predetermined intervals in order to prolong the life of the unit. The circuit is a low-power communications or telemetry device. Certain frequencies are reserved for devices of this type, as for example, the 38 to 41 Mgz. frequencies are reserved for biomedical transmissions. Reference is made to 47 C.F.R. §15. It will be also obvious to those skilled in the art that other types of transmitting devices may be used, such as induction transmitters or those operating in the ultra sonic ranges.

Figure 3:
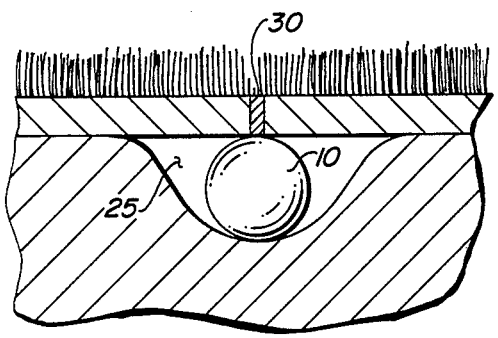
FIG. 3 is a detail view of a portion of a calf's head showing the encapsulated transmitter implanted therein.

Capsule 10 may be placed in any suitable location in the animal and may be placed subcutaneously or in an incision made for this purpose. The capsule may also be ingested and inserted by a balling gun or similar instrument. A particularly suitable location for this purpose in cattle is a cavity which exists at the base of the skull of cattle. As shown in FIG. 3, cavity 25 is approximately two inches by two inches and contains primarily fatty tissue. This area is generally by the posterior border of the conchal cartilege and caudally by the posterior border of the cleido-occipitalis muscle.

An incision 30 is made in this area and the capsule inserted. The fatty tissue easily receives the capsule with minimum of discomfort and bleeding. The incision will heal over quickly in a short period of time so that the capsule will not become dislodged and will provide an accurate indication of the deep body temperature of the animal Capsule 10 may be inserted manually or may be inserted by means of an implantation device having a spring-loaded ejector which forces the capsule in place through a barrel. Similar devices are used for implantation of time-release capsules which contain an insecticide to protect the animal from pests. For example, reference is made to U.S. Pat. Nos. 2,632,444 and 2,850,013 which show devices which could be adapted for this use.

Figure 4:
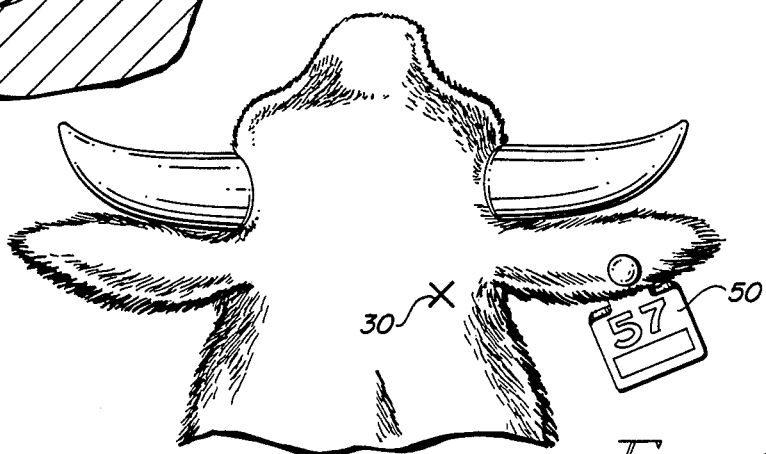
FIG. 4 is a top view of a calf's head showing the in vivo implant site and the adjacent receiver in connection with an ear tag assembly.

The receiver 14 is located on the animal proximate the location 30 of the transmitter and, as shown in FIG. 4, the ear of the animal has been found to be a particularly satisfactory place to locate the receiver as part of an identification tag 50. For identification purposes, this location provides high visibility to the attendant monitoring the animals. The receiver 40 is shown schematically in FIG. 2 and includes a threshold detector 22 which activates the receiver only when a signal of predetermined value is received from sensor 20. The coded signal from signal generator 26 is periodically sent to the receiver and may be also used as an operational verification signal.

The animal tag is generally designated as 50 and is a two-component tag and is shown in FIGS. 5 and 6. Such tags include a male portion which is passed through the ear of the animal and is mated with a female portion. The tag includes a female tag body component generally designated by the numeral 52 having a neck portion 54 and a body portion 56. The upper a reduced neck portion 54 defines an aperture 55. A locking insert 60 or male portion has a projection or pin 61 with an enlarged head 62 which is received within aperture 55 and retained therein when the tag is in place. Ear tags of this general type are well known and are typically made of thermoplastic material such as flexible polyvinylchloride and applied by hand-held applicators which by manual application of force causes the male portion 60 to be passed through the ear and mated with the female portion as shown in FIG. 4.

The body 56 of the female component 50 houses the receiver 14 and a power source 62 as seen in FIGS. 5 and 6. The receiver is operatively connected to a pair of visual indicator devices 66 and 68. Visual indicator devices 66 and 68 may typically LED's with indicator 66 being white and indicator 68 being red. In the normal mode of operation, light 66 will provide a visual indication and verification that the device is functional, as for example by flashing white either continuously or periodically upon receipt of a signal from the signal generator. Upon indication that temperature has exceeded a pre-determined level, a visual change will take place on the receiving device as visual indicator 68 will now flash red. This condition will continue until re-set or turned off.

As shown in FIGS. 7 and 8, the visual indication of an alarm condition can be provided by means other than a flashing light. In FIG. 7, an animal tag again is shown as a two-component tag having a female tag portion 70 with a body 72 and a neck portion 74 defining an aperture 75. Aperture 75 will receive the male component 76 of the tag which is inserted through the animal's ear. The body of the tag is provided with alphanumerical identification indicia 78 as is conventional. The body 72 of the tag includes a pair of opposed locking pins 80 and 81 which support a transversely extending chemically treated wire 84 which is disposed immediately adjacent chemically sensitive indictor area 85. The body portion of the tag also defines a housing or compartment 86 for a battery 88 associated circuitry and a receiver 14 adapted to receive signals from the adjacent implanted transmitter.

Wire 84 is a nichrome or similar wire coated with a suitable chemical such as chlorine or ammonia and is connected in a resistance circuit connected to the battery 88. When receiver 14 triggers due to a signal from the implanted transmitter due to an increase in temperature above a predetermined level, the resistance circuit is actuated. Heating of the nichrome wire 84 will heat the chemical coating, releasing a suitable chemical substance such as chlorine or ammonia which is reactive with the area 85 causing the area to undergo a physical change, such as a change of color. The change of color serves as a visual indication to the operators of a possible diseased condition in an animal.

FIG. 9 shows still another embodiment of ear tag providing a visual indication of an elevated temperature condition in an animal. Ear tag portion 100 is adapted to be secured to the ear of the animal at aperture 102 by male portion 104. The body 105 of the ear tag is provided with indicia 106 such as the identification number of the animal. Body 105 also defines a compartment 108 to contain the receiver, power source and associated circuitry. An area 110 of the tag is provided with a highly visible color on an indicator section such as a flourescent orange or other bright color. The color area is normally covered or protected by a releasable covering 112 which is secured to the body of the tag along the lower horizontal edge 114 at the lower edge of area 110. The covering 112 is configured having "memory" so that it will tend to assume a rolled-up position near the bottom of the tag revealing the subjacent color area 110. In the assembled position, the covering 112 obscures area 110 and is held in place at the upper horizontal edge by a thin nichrome wire 120 in which the position of the area 110 is obscured from view. The nichrome wire 120 is connected in a resistance circuit connected to a battery. An increase in temperature sensed at the implanted capsule will cause a signal to be sent to the receiver 14 within housing 108 actuating the resistance circuit thus heating wire 120. The increase in temperature in the wire will slice or otherwise cut through the material of the covering 112 allowing it to pull away from the subjacent color patch so that the area 110 is now in view of the attendant providing a visual indication of possibly diseased condition.

In FIG. 9 the covering is shown in a partially released position. Note the circuitry of the resistance circuit is well known and detailed description thereof is not believed necessary. The same power source utilized for the receiver may also be used in the resistance circuit.

While the preferred location of the receiver 14 is on an ear tag assembly in the case of cattle, other locations proximate the transmitter may also be used. For example, an animal can be fitted with a collar or halter containing these components.

It will be obvious to those skilled in the art that in addition to the visual alarm, various audible alarms may also be associated with the ear tag. For example, the receipt of a signal by the receiver associated with the ear tag could trigger operation of an alarm bell or the like.

As an added feature, a repeater transmitter 17 may be incorporated in the receiver device 14 to increase the distance of alarm warning from proximate the animal to a remote location as shown in FIG. 2. The re-transmitter 17 is located on the animal, as for example as part of the ear tag in which the receiver is located. The re-transmitter generally operates at a higher power level and it may be necessary to secure licensing for such re-transmissions. The advantage is that the re-transmission data can be received at an off-site location and can be collected and retained by a computerized monitor for later use. The re-transmitted signal will include the unique identification number from the signal generator thereby providing the animal with a unique internal brand for purposes of identification of ownership to discourage theft and to provide owner identification particularly when animals are contained in large mixed herds.

Straying of animals is also another problem on open ranges. The internal implanted transmitter will assist in locating stray animals. As shown in FIG. 10, a handheld locator interrogator 150 can be provided which will send a signal or interrogate the receiver 14. As a result, a higher power signal will be sent by re-transmitter 17. This signal can be remotely received and through simple triangulation procedures, the location of the animal can be determined.

FIGS. 11, 12 and 13 show still another embodiment of an ear tag adapted to house the receiver, power supply and re-transmitter. Again, the device consists of a female ear tag portion 160 having an enlarged body 162 with appropriate indicia 165 thereon. The body defines an integrally formed male projection 170 having an enlarged conical head 172. The retainer 180 has a series of internally formed saw-like projections which when engaged with the conical head 172 will note allow the pin to withdraw. When the unit is to be recovered, pin 172 is severed and the main tag component 160 is returned to a designated location for re-working for reuse. Again, the female portion of the tag carries appropriate housing for radio receiver, power supply and visual indicator.

From the foregoing, it will be seen the present invention achieves the primary objectives of the invention and provides an implantable transmitting device which can be placed beneath the surface of the animal and allow the incision to heal. The device can work for an extended period of time and is recoverable from the animal when the animal is processed. The transmitter tag can be removed and sent to a central recycling or refurbishing unit for repair and replacement of the battery if necessary. The refurbished units can then be provided to the cattle operator for reuse.

It will be obvious to those skilled in the art to make various changes, alterations and modifications to the telltale monitoring system described above. To the extent such changes, alterations and modifications do not depart from the spirit and scope of the appended claims, they are intended to be encompassed therein.

I claim:

1. An implantable telltale monitoring system for measuring a physiological parameter in an animal comprising:
   (a) a housing containing circuit means, said circuit means including a sensor for monitoring said parameter and operatively connected to a transmitter within said housing which emits a signal representative of the measured parameter of a predetermined magnitude, said housing configured to be placed at an implantable location on the animal; and
   (b) a receiver unit having attachment means adapted to secure the receiver unit to the animal at a location proximate the transmitter and further including indicating means, said indicating means responsive to said signal received by said receiver unit and emitted by said transmitter to provide a localized indication perceivable by an attendant of said measured parameter being of said predetermined magnitude.

2. The monitoring system of claim 1 wherein said housing is fabricated from a biomedically acceptable plastic material and further wherein said housing is generally capsule-shaped to be implanted within the animal.

3. The monitoring system of claim 2 wherein said housing is provided with a cutting edge.

4. The monitoring system of claim 1 wherein said attachment means comprises a two-component ear tag.

5. The monitoring system of claim 1 wherein said circuit means includes a timer and threshold detection means whereby said transmitter is pulsed at predetermined intervals and is activated if said predetermined magnitude of said measured parameter is sensed.

6. The monitoring system of claim 5 further including signal generating means providing an encoded digital identification signal at predetermined intervals to said transmitter.

7. The monitoring system of claim 6 wherein said transmitter is a low power transmitter.

8. The monitoring system of claim 1 wherein said receiver unit further includes repeater transmitter means associated with said receiver unit and adapted to re-transmit a signal to a remote location when said receiver unit is actuated.

9. The monitoring system of claim 1 wherein said indicating means comprises a light and further including visual means for verifying the operability of said system.

10. The monitoring system of claim 1 wherein said indicating means includes a circuit on said attachment means having a temperature sensing element which is activated upon receipt of said signal at said receiver unit and which element actuates said indicating means.

11. The monitoring system of claim 10 wherein said indicating means includes a chemically sensitive area and heating means adjacent thereto, said heating means being actuable to cause a chemical change at said chemically sensitive area when said signal is received.

12. The monitoring system of claim 10 wherein said indicating means comprises an area defining a high visibility surface and an opaque protective cover overlying said surface and means responsive to said signal to remove said cover from said surface.

13. A method of telltale animal monitoring for monitoring a physiological parameter in an animal comprising:
   (a) providing monitoring means in an encapsulated housing, said monitoring means including sensor means and a transmitter operatively connected to said sensor means and adapted to emit a signal representative of a predetermined value of the physiological parameter being monitored;
   (b) implanting said encapsulated housing in an incision in the animal and thereafter closing the incision and allowing the incision to heal;
   (c) monitoring said signal at a receiver at a location on said animal proximate said transmitter; and
   (d) providing a perceptible indication of said signal at the receiver when the signal reaches said predetermined value.

14. The method of claim 13 further including the steps of recovering said monitoring means from said animal and refurbishing said monitoring means for reuse.

15. The method of claim 13 wherein said incision is made in the area generally defined by the posterior border of the conchal cartilege and caudally by the posterior border of the cleido-occipitalis muscle.

* * * * *